United States Patent [19]
Kas et al.

[11] Patent Number: 6,063,929
[45] Date of Patent: May 16, 2000

[54] METHOD TO PREPARE DIHYDROTHIAZOLES

[75] Inventors: Kathleen Anne Kas, Lindenwold, N.J.; Aaron Sarafinas, Ivyland; Randall Wayne Stephens, Perkasie, both of Pa.

[73] Assignee: Rohm and Haas Company, Philadelphia, Pa.

[21] Appl. No.: 09/241,901

[22] Filed: Feb. 2, 1999

Related U.S. Application Data

[60] Provisional application No. 60/074,512, Feb. 13, 1998.
[51] Int. Cl.⁷ .................................................. C07D 417/04
[52] U.S. Cl. ............................................................. 546/270.4
[58] Field of Search ........................................... 546/270.4

[56] References Cited

U.S. PATENT DOCUMENTS

| | | |
|---|---|---|
| 2,474,426 | 6/1949 | Kendall et al. . |
| 4,988,384 | 1/1991 | Sing et al. . |
| 5,100,461 | 3/1992 | Sing et al. . |

OTHER PUBLICATIONS

Djerassi, C. et al., *Journal of Organic Chemistry*, 1950, vol. 15, 694–699.

Babcock, S.H. et al., *Journal of the American Chemical Society*, 1937, vol. 59, 2260–2261.

*Primary Examiner*—Laura L. Stockton
*Attorney, Agent, or Firm*—Thomas D. Rogerson

[57] ABSTRACT

The present invention relates to a method to prepare 2-pyridyl substituted dihydrothiazoles.

9 Claims, No Drawings

METHOD TO PREPARE DIHYDROTHIAZOLES

This application claims the benefit of U.S. Provisional Application No. 60/074,512 filed Feb. 13, 1998.

The present invention relates to a method to prepare 2-(3-pyridyl)-substituted 4,5-dihydrothiazoles.

U.S. Pat. No. 4,988,384 discloses a class of substituted pyridine compounds of the formula:

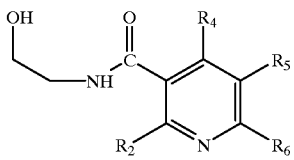

I which may be converted to 4,5-dihydro-2-(3-pyridyl)-thiazoles of the formula:

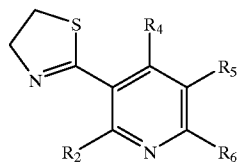

wherein:
$R_2$ and $R_6$ are independently fluorinated methyl, chlorofluorinated methyl, chlorinated methyl, or lower alkyl;
$R_4$ is ($C_1$–$C_4$) straight or branched chain alkyl, $C_3$–$C_4$ cycloalkyl, cycloalkylalkyl, alkylthioalkyl, or bis(alkylthio)alkyl;
$R_5$ is cyano or

wherein $Z_1$ is O, S, or $NR_7$ wherein $R_7$ is lower alkyl and $Z_2$ is alkoxy, alkenoxy, alkynoxy, alkylthio, pyrazolyl, haloalkoxy, cyanoalkoxy, chloro and —$NHR_8$ wherein $R_8$ is lower alkyl;
by reacting a mixture of the hydroxyalkylaminocarbonyl substituted pyridine with phosphorous pentasulfide ($P_2S_5$) in a solvent at reflux temperatures.

Alternatively, ring closures of this type have also been carried out by reacting $P_2S_5$ with haloalkylamides. Processes for the cyclization N-(2-bromoethyl)-, or N-(3-bromopropyl)aryloxyacetamides to afford dihydrothiazoles and penthiazolines respectively have been described in Djerassi, C. et.al. Journal of Organic Chemistry 1950, 15, 694. Similarly, N-(2-bromoethyl)-, or N-(3-bromopropyl) benzamides have been cyclized as described in Adam, R. et. al. Journal of the American Chemical Society 1937, 59, 2260. The cyclization of N-(3-bromopropyl) amide derivatives of nicotinic acid have similarly been reacted as described in U.S. Pat. No. 5,100,461.

Although the reaction of haloalkylamides derived from compounds of formula I with $P_2S_5$ works reasonably well when the total volume of the mixture is at a laboratory scale, for example, less than 22 liters, at larger volumes the overall yield of the 4,5-dihydro-2-(3-pyridyl)-thiazole decreases. We have discovered that by degassing the refluxing mixture, the yield is significantly enhanced.

The present invention is a method to prepare 4,5-dihydro-2-(3-pyridyl)-thiazoles, comprising the steps of:
a) heating a mixture of a compound of the formula II:

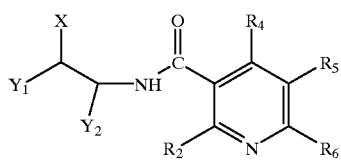

II wherein
X is chloro, bromo, iodo, thiol, or hydroxy;
$Y_1$ and $Y_2$ and independently hydrogen or alkyl;
$R_2$, $R_4$, $R_5$, and $R_6$ are independently hydrogen, halo, alkyl, alkenyl, alkynyl, cycloalkyl, cycloaklylalkyl, alkylthioalkyl, bis(alkylthio)alkyl, cyano, fluorinated methyl, chlorofluorinated methyl, chlorinated methyl,

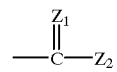

wherein $Z_1$ is O, S, or $NR_7$ wherein $R_7$ is alkyl and $Z_2$ is alkoxy, alkenoxy, alkynoxy, alkylthio, pyrazolyl, haloalkoxy, cyanoalkoxy, chloro or —$NHR_8$ wherein $R_8$ is lower alkyl;
and $P_2S_5$ in a solvent at reflux; and
b) degassing the mixture while heating.

The term "alkyl" means both straight and branched chain ($C_1$–$C_7$) radicals which include, for example, methyl, ethyl, n-propyl, isopropyl, 1-ethylpropyl, n-butyl, tert-butyl, isobutyl, 2,2-dimethylpropyl, pentyl, and the like. The terms "alkenyl" and "alkynyl" mean ($C_3$–$C_7$) alkenyl and alkynyl groups such as, for example, 2-propenyl, 2-butenyl, 3-butenyl, 2-methyl-2-propenyl, 2-propynyl, and the like. The term "cycloalkylalkyl" means a ($C_1$–$C_2$) alkyl group substituted with a ($C_3$–$C_6$) cycloalkyl group such as, for example cyclopropylmethyl, cyclopropylethyl, cyclobutylmethyl, cyclopentylethyl, and the like. The terms "fluorinated methyl", "chlorinated methyl", and chlorofluorinated methyl" mean methyl radicals wherein one or more of the three hydrogen atoms have been replaced by a fluorine atom, a chlorine atom, or a fluorine atom and a chlorine atom, respectively.

Preferably, in the compound of formula II, X is chloro or hydroxy; one of $R_2$ and $R_6$ is $CF_3$ and the other is $CF_2H$; $R_4$ is a $C_3$–$C_7$ branched chain alkyl; and $R_5$ is methoxycarbonyl or methoxythiocarbonyl. More preferably, X is chloro, $R_2$ is $CF_3$, $R_6$ is $CF_2H$, $R_4$ is 2-methylpropyl, and $R_5$ is methoxycarbonyl.

The degassing step may be accomplished using any one or more degassing processes known to those skilled in the art. Preferably, degassing is accomplished by rapid mechanical agitation of the mixture, by sparging the mixture using a gas which does not itself react with the reactants, product, or solvent in the mixture, by subjecting the mixture to a rapid boil-up, or by a combination of one or more of these methods. Degassing may also be accomplished by subjecting the mixture to a mild vacuum while maintaining reflux. More preferably, degassing is accomplished by sparging the mixture or by subjecting the mixture to rapid boil-up. Most preferably, degassing is accomplished by sparging the mixture and subjecting the mixture to rapid boil-up with high agitation rates. Preferred sparging gasses include nitrogen, helium, and argon.

The term "sparging" means to agitate the mixture by forcing a gas into the mixture through a line having one or more perforations or nozzles. The term "rapid boil-up" means to reflux with high heat flux and high vaporization rate. That is, reflux at a rolling boil of the mixture. The term "high agitation rates" means agitation rates that are sufficient to suspend the $P_2S_5$, disperse any sparged gas, and maintain high process-side heat transfer coefficients.

The solvent employed in the reaction is not critical. However, it must be a solvent which is inert to the reactants, reaction products, and the conditions of the reaction. Acceptable solvents include, for example, ethers, alkanes, substituted alkanes, aromatic, and substituted aromatic compounds. Preferred solvents are polar solvents such as ethers and substituted aromatic compounds. More preferred solvents are substituted aromatic compounds such as, for example, toluene, o, m, or p-xylene, chlorobenzene, and o, m, or p-dichlorobenzene. The most preferred solvent is chlorobenzene.

The order of addition of the reactants to the solvent is not critical. However, it is preferred that the solvent and halo or hydroxy alkylaminocarbonyl substituted pyridine be combined and then the $P_2S_5$ be added. Most preferably, the $P_2S_5$ is added after the remaining mixture components are at a high temperature. Thus, the preferred process is to combine the solvent and the substituted pyridine, heat the mixture until it is near or at reflux, and then add the $P_2S_5$; most preferably under high rates of agitation.

The method of this invention is illustrated by the following examples and comparative examples. In the following examples, all percentages and parts are by weight.

EXAMPLE 1

Base Conditions

Comparison Example

This example was conducted in a glass-lined vessel with a retreat blade agitator at 42 rpm, hot oil system on the vessel jacket, overhead condenser and reflux line, and a recirculation line. Prior to the reaction, a crude mixture of methyl 2-(difluoromethyl)-5-(((2-chloroethyl)amino)carbonyl)-4-(2-methylpropyl)-6-trifluoromethyl)-3-pyridinecarboxylate was dried by azeotropic distillation by heating to 80° C. under vacuum to 150 mm of Hg to remove water This mixture, containing 25 parts of methyl 2-(difluoromethyl)-5-(((2-chloroethyl)amino)carbonyl)-4-(2-methylpropyl)-6-trifluoromethyl)-3-pyridinecarboxylate in 75 parts of chlorobenzene solvent, was then heated to 90° C., at which time 3.72 parts of phosphorus pentasulfide was then charged. The batch was heated to a gentle reflux and recirculated. The reaction was monitored by gas chromatography (GC) for reaction completion. When the reaction was complete, the reaction mixture was washed successively with 68 parts of water, 40 parts of 5% aqueous sodium hydroxide solution, 5.91 parts of 15% aqueous sodium hypochlorite in 60 parts of water, followed by a final wash with 45 parts of water. The product was then transferred to another glass-lined vessel, where the residual water and chlorobenzene solvent was removed via steam sparging and distillation at approximately 100° C. and approximately 70 mm of mercury. The yield of methyl 2-(difluoromethyl)-5-(4,5-dihydro-2-thiazolyl)-4-(2-methylpropyl)-6-(trifluoromethyl)-3-pyridinecarboxylate was 78% of 85.7% pure product.

EXAMPLE 2

Closed Conditions to Impede Degassing

This example was conducted in the same manner as example 1 except that the agitator was at 100 rpm and 3.8 parts of $P_2S_5$ was added at 128° C. The resulting mixture was then heated to a gentle reflux while maintaining a pressure of 150–260 mm mercury on the reactor throughout the reaction. The batch was recirculated and reaction completion samples were taken from the recirculation loop. The reaction was monitored by gas chromatography (GC) for reaction completion. When complete, the reaction mixture was washed sequentially with 70 parts of water, 30 parts of water along with 15 parts of 5% aqueous sodium hydroxide solution, 5.9 parts of 15% aqueous sodium hypochlorite in 60 parts of water, followed by a final wash with 45 parts of water. The product was then transferred to a glass-lined vessel, where the residual water and chlorobenzene solvent was removed via steam sparging and distillation at 98° C. and 71 mm of mercury. In this case, the yield was 73%.of 83.8% pure product.

EXAMPLE 3

Sparging Conditions

This example was conducted the same as example 2 except that 3.93 parts of phosphorus pentasulfide was added. The resulting mixture was heated to a gentle reflux and nitrogen was introduced into the bottom of the reactor to sparge the mixture. The batch was recirculated for 10–15 minutes every hour prior to sampling. The reaction was monitored by gas chromatography (GC) for reaction completion. When complete, the reaction mixture was successively washed with 70 parts of water, 30 parts of water along with 10 parts of 5% aqueous sodium hydroxide solution, 6.41 parts of 15% aqueous sodium hypochlorite in 60 parts of water, followed by a final wash with 45 parts of water. The product was then transferred to a glass-lined vessel, where the residual water and chlorobenzene solvent was removed via steam sparging and distillation at 98° C. and 28 inches of mercury. In this case, the yield was 82%.of 86.9% pure product.

EXAMPLE 4

High Boil-up Conditions

This example was conducted the same as example 2 except that 3.83 parts of phosphorus pentasulfide was added. The resulting mixture was then heated at rapid boil-up. The reaction was monitored by gas chromatography (GC) for reaction completion. The reaction mixture was then washed as in example 2 The product was then transferred to a glass-lined vessel, where the residual water and chlorobenzene solvent was removed via steam sparging and distillation at 98° C. and 28 inches of mercury. In this case, the yield was 86%.of 90.8% pure product.

EXAMPLE 5

High Boil-up with Sparging

This example was conducted the same as example 2 except that the agitator was run at 120 rpm, a higher capacity hot oil system was used on the vessel jacket, the mixture was heated to a gentle reflux with a jacket temperature of 138° C., and then 3.81 parts of phosphorus pentasulfide was added. The batch was then heated to a rapid boil-up and nitrogen was introduced into the bottom of the reactor to sparge the mixture. The reaction was monitored by gas chromatography (GC) for reaction completion. When complete, the reaction mixture was washed successively with 70 parts of water, 30 parts of water along with 40 parts of 5% aqueous sodium hydroxide solution, 5.91 parts of 15% aqueous sodium hypochlorite in 46 parts of water, followed by a final wash with 45 parts of water. The product was then transferred to a glass-lined vessel, where the residual water and chlorobenzene solvent was removed via steam sparging and distillation at 92° C. and 28 inches of mercury. In this case, the yield was 89%.of 91% pure product.

The following examples demonstrate the effect of boil-up rate on the rate of reaction. At higher boil-up rates with the resulting improved degassing, the reaction goes to completion more rapidly even though the reaction temperature remains constant. In all cases, the reaction resulted in a greater than 99% conversion to the dihydrothiazole product.

EXAMPLE 6

To a jacketed glass reactor equipped with an overhead stir motor, reflux condenser and thermocouple was charged 165.3 g of methyl 2-(difluoromethyl)-5-(((2-chloroethyl)amino)carbonyl)-4-(2-methylpropyl)-6-trifluoromethyl)-3-pyridinecarboxylate and 471.5 g of chlorobenzene. The mixture was heated to 80° C. at which time 23.45 g of phosphorous pentasulfide was added. The reaction mixture was heated to reflux with a rapid boil-up rate using a jacket temperature of 170° C. with an average pot temperature of 136° C. The reaction was monitored by gas chromatography (GC) and judged to be complete after 3 h. The reaction mixture was cooled to less than 100° C., and then successively washed with water, dilute caustic solution, dilute bleach, and finally with water. The product was isolated as a brown oil that solidified on standing.

EXAMPLE 7

This example was conducted as described in 6 except using a jacket temperature of 160° C. with an average pot temperature of 136° C., this reaction was judged to be complete after 4.7 h.

EXAMPLE 8

This example was conducted as described in Example 6 except using a jacket temperature of 150° C. with an average pot temperature of 134° C., this reaction was judged to be complete after 5.5 h.

We claim:

1. A method to prepare a 4,5-dihydro-2-(3-pyridyl)-thiazole, comprising the steps of:

a) heating a mixture of a compound of the formula:

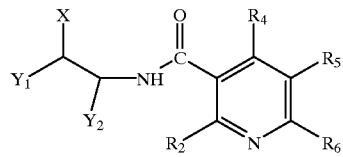

wherein
X is chloro, bromo, iodo, thiol, or hydroxy;
$Y_1$ and $Y_2$ and independently hydrogen or alkyl;
$R_2$, $R_4$, $R_5$, and $R_6$ are independently hydrogen, halo, alkyl, alkenyl, alkynyl, cycloalkyl, cycloaklylalkyl, alkylthioalkyl, bis(alkylthio)alkyl, cyano, fluorinated methyl, chlorofluorinated methyl, chlorinated methyl, or

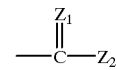

wherein $Z_1$ is O, S, or $NR_7$ wherein $R_7$ is alkyl and $Z_2$ is alkoxy, alkenoxy, alkynoxy, alkylthio, pyrazolyl, haloalkoxy, cyanoalkoxy, chloro or —$NHR_8$ wherein $R_8$ is lower alkyl;
and $P_2S_5$ in a solvent at reflux; and b) degassing the mixture while heating.

2. The method of claim 1 wherein the degassing step is accomplished by agitating the mixture at high agitation rates.

3. The method of claim 1 wherein the degassing step is accomplished by rapid boil-up of the mixture at reflux temperature.

4. The method of claim 1 wherein the degassing step is accomplished by sparging the mixture with a gas which does not otherwise interfere with the reaction.

5. The method of claim 1 wherein the degassing step is accomplished by rapid boil-up of the mixture at reflux temperature, sparging the mixture with a gas which does not otherwise interfere with the reaction, and rapid agitation of the mixture.

6. The method of claim 1 wherein the compound of the mixture is of the formula:

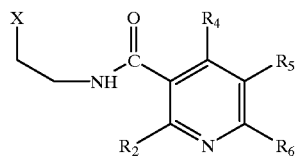

wherein
X is chloro, thiol, or hydroxy;
one of $R_2$ and $R_6$ is $CF_3$ and the other is $CF_2H$;
$R_4$ is a $C_3$–$C_7$ branched chain alkyl; and
$R_5$ is methoxycarbonyl or methoxythiocarbonyl.

7. The method of claim 1 wherein the compound of the mixture is of the formula:

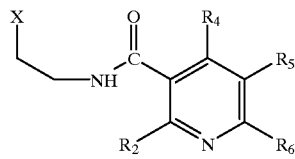

wherein
X is chloro;
$R_2$ is $CF_3$;
$R_6$ is $CF_2H$;
$R_4$ is 2-methylpropyl; and
$R_5$ is methoxycarbonyl.

8. The method of claim 1 wherein the solvent is selected from ethers and substituted aromatic compounds.

9. The method of claim 4 wherein the gas is selected from nitrogen, helium, and argon.

* * * * *